United States Patent [19]

Klaubert et al.

[11] Patent Number: 4,495,101

[45] Date of Patent: Jan. 22, 1985

[54] ANTIINFLAMMATORY 5H-TETRAZOLO (5,1-C)(1,4)BENZODIAZEPINE DERIVATIVES

[75] Inventors: Dieter H. Klaubert, Flemington, N.J.; Stanley C. Bell, Narberth, Pa.; Thomas W. Pattison, King of Prussia, Pa.; Richard W. Rees, Bryn Mawr, Pa.

[73] Assignee: American Home Products Corporation, New York, N.Y.

[21] Appl. No.: 489,655

[22] Filed: Apr. 28, 1983

[51] Int. Cl.³ ............... C07D 210/00; C07D 403/00
[52] U.S. Cl. ...................... 260/239.3 T; 260/243.3; 260/244.4; 260/245.5; 544/366
[58] Field of Search .............. 544/366; 260/245.5, 260/239.3, 243.3, 244.4

[56] References Cited

U.S. PATENT DOCUMENTS 3,717,653  2/1973  Hester .................... 260/308 D

OTHER PUBLICATIONS

Peet et al., J. Heterocyclic Chem. 14, 561 (1977), Chem. Abst. vol. 87, 1977, p. 591, 152154n.

Hester et al., Tet. Letters No. 20, 1609–1612 (1971).
Madronero et al., J. Heterocyclic Chem. 15, 1127 (1978).

*Primary Examiner*—Donald G. Daus
*Assistant Examiner*—Cecilia Shen
*Attorney, Agent, or Firm*—Richard K. Jackson

[57] ABSTRACT

The compounds of the formula

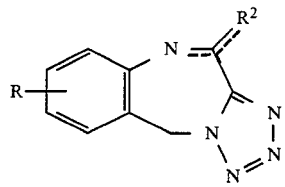

in which
R is hydrogen, halogen, alkyl, alkoxy, hydroxyl, nitro or cyano; and
$R^2$ is =O, =S, $H_2$, —$SCH_3$, or an amino group; with the proviso that when R is chloro in 8-position, $R^2$ must be other than oxygen or sulfur; or a pharmaceutically acceptable salt thereof.

20 Claims, No Drawings

ANTIINFLAMMATORY 5H-TETRAZOLO (5,1-C)(1,4)BENZODIAZEPINE DERIVATIVES

BACKGROUND OF THE INVENTION

Hester et al., Tetrahedron Letters, No. 20, pp. 1609–1612 (1971) disclose several 1,4-benzodiazepines with heterocyclic groups fused on the "a" and "d" benzodiazepine faces. The 6-phenyl-4H-tetrazolo-[1,4-a][1,4]benzodiazepines are said to be sedatives and tranquilizers (U.S. Pat. No. 3,717,653). Peet et al., J. Het. Chem. 14 561 (1977) disclose 5H-tetrazolo[1,5-d][1,4]benzodiazepin-6(7H)-one derivatives and Madronero et al., J. Het. Chem., 15 1127 (1978) discloses tetrazolo-[1,5-d][1,4]benzodiazepine derivatives (the designation of Compound VIII on page 1127 as a tetrazolo [1,5-a]-derivative is in error because the face of attachment is "d").

BRIEF DESCRIPTION OF THE INVENTION

In accordance with this invention there is provided a group of 5H-tetrazolo[5,1-c][1,4]benzodiazepines which are antiinflammatory agents useful in the treatment of inflammation which accompanies various disease states such as arthritis.

DETAILED DESCRIPTION OF THE INVENTION

The novel ring system presented by the 5H-tetrazolo[5,1-c][1,4]benzodiazepines of this invention is represented by the following structural formula:

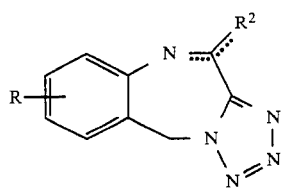

in which
R is hydrogen, halogen, alkyl of 1 to 6 carbon atoms, alkoxy of 1 to 6 carbon atoms, hydroxyl or cyano; and
$R^2$ is $=O$, $=S$, $H_2$, $-SCH_3$, or $-NR^4R^5$
where $R^4$ and $R^5$ are, independently, hydrogen, alkyl of 1 to 6 carbon atoms or dialkylaminoalkyl where each alkyl moiety contains 1 to 6 carbon atoms, or $R^4$ and $R^5$ together form an alkylidene group of 4 to 6 carbon atoms, or, together with the nitrogen atom to which they are attached, they form the 4-morpholinyl moiety or a radical of the formula:

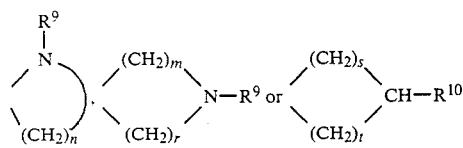

wherein $R^9$ is alkyl of 1 to 6 carbon atoms, aryl of 6 to 10 carbon atoms, hydroxyalkyl of 1 to 6 carbon atoms; aralkyl of 7 to 16 carbon atoms or alkoxyalkyl of 2 to 12 carbon atoms; $R^{10}$ is alkylamino of 1 to 6 carbon atoms or piperidino; n is one of the integers 3, 4 or 5; m is one of the integers 1 or 2; r is one of the integers 2 or 3; s is an integer from 0 to 6; t is an integer from 0 to 6; with the proviso that the sum of s and t is 3 to 6; and with the proviso that when R is chloro in 8-position, $R^2$ must be other than oxygen or sulfur; or a pharmaceutically acceptable salt thereof.

In the preceding structural formula depicting the compounds of this invention, the dotted lines represent optional unsaturation within the ring and mandatory unsaturation when $R^2$ is oxygen or sulfur. It is generally preferred that the halo substituent be chlorine, bromine or fluorine although iodine is acceptable. Likewise, it is preferred that the alkyl and alkoxy substituents be relatively small, the methyl, ethyl, propyl, isopropyl, methoxy, ethoxy, propoxy and isopropoxy groups being preferred. The pharmaceutically acceptable salts are those formed with acids conventionally employed in the medicinal art for that purpose. Those particularly suitable include hydrohalic, sulfuric or phosphoric acids, nitric or perchloric acid, formic, acetic, propionic, oxalic, succinic, glycollic, lactic, malic, tartaric, citric, ascorbic, maleic, hydroxymaleic, dihydroxymaleic, or pyruvic acid; phenylacetic, benzoic, para-aminobenzoic, anthranilic, para-hydroxybenzoic, salicyclic or para-aminosalicylic acid, methanesulfonic, ethanesulfonic, hydroxy ethanesulfonic, toluenesulfonic, naphthalenesulfonic acids, sulfanilic acid.

The substituent "R" preferably appears in position 7 or 8 of the benzene ring.

The most preferred compounds of this invention are depicted by the structural formula

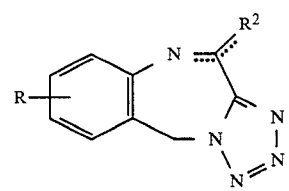

in which
R is hydrogen, chloro, methyl or nitro; and $R^2$ is $=O$, $=S$, $H_2$, $-SCH_3$, $-NHCH_2CH_2N<CH_3$, $<CH_3$

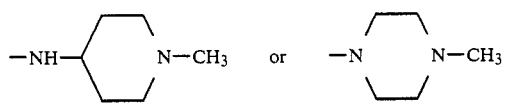

with the proviso that when R is chloro in 8-position, $R^2$ must be other than oxygen or sulfur; or a pharmaceutically acceptable salt thereof.

The compounds of this invention are produced by reaction of an appropriately substituted ortho-nitrobenzylchloride with sodium azide to produce

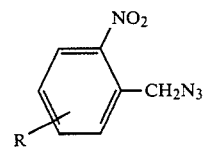

which is condensed with a lower alkyl cyano formate (following the procedure disclosed by Katner in U.S. Pat. No. 3,962,272) while heating to about 100°–140° C. in a Teflon ® lined bomb to give

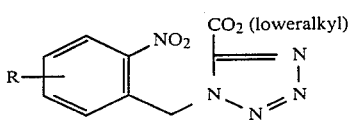

Reduction of the nitro group with iron in ethanolic HCl followed by ring closure (trimethylaluminum in methylene chloride and hexane) forms the lactam:

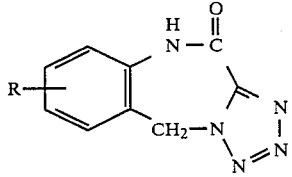

The lactam is readily reduced by LiAlH₄ to afford the amines

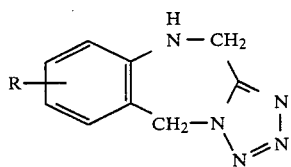

The corresponding thiolactam is readily obtained by heating the lactam with phosphorous pentasulfide. The amidine derivatives are produced by conversion of the thiolactam to a thioimidate with methyl iodide followed by reaction with an appropriate amine to displace the alkylamercapto substituent.

Nitration of the lactams with nitric acid in sulfuric acid provides a nitro substituent at 7-position of the aromatic ring. Other substitutional variations, involving non-functional groups, are readily carried through the preparatory reaction sequence when present in the ortho-nitrobenzylchloride reactant.

The anti-inflammatory activity of the claimed compounds was established by direct measurement of the effect of structurally representative compounds in the rat carrageenan edema test. This standard pharmacological procedure for determining antiinflammatory effects of a compound is performed by subcutaneous injection in the right paw of 6 animals (140–180 grams, male Sprague-Dawley or Charles River rats) with 0.1 milliliter of 1 percent carrageenan at zero time. The compounds representative of this invention are administered orally one hour prior to carrageenan at 150 milligrams per kilogram. The paw volume (edema in milliliters) is determined at zero time and three hours after carrageenan administration by mercury plethysmographic readings (milliliter) of the paw. From the change in paw volume compared to control, the percent inhibition of edema is determined. The results obtained with the compounds of Examples 1, 9, 17 and 18, which are representative of the other compounds of the invention, are as follows:

| Compound | % Inhibition of Edema |
| --- | --- |
| Example 1 | 39** |
| Example 9 | 42** |
| Example 17 | 42** |

-continued

| Compound | % Inhibition of Edema |
| --- | --- |
| Example 18 | 33* |

*$p \leq 0.05$
**$p \leq 0.01$

Based upon the results of these experiments, it can be seen that the compounds of this invention are anti-inflammatory agents. As such, they are useful in treatment of those inflammatory states requiring chronic treatment, such as rheumatoid arthritis and the like.

The compounds of the invention can be formulated as anti-inflammatory agents, into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The compounds may be encapsulated with or without other carriers. In all cases the proportion of active ingredients in said compositions both solid and liquid will be at least sufficient to impart anti-inflammatory activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration level that will generally afford effective results without causing any harmful or deleterious side effects. With large animals (about 70 kg. body weight), for oral administration the dose is from about 150 milligrams to about 300 milligrams as a single unit dose administered from one to four times per day as needed.

The following examples are presented to illustrate the method employed to produce the compounds of this invention.

EXAMPLE 1

7-Chloro-5,10-dihydro-11H-tetrazolo[5,1-c][1,4]-benzodiazepine-11-one

To 70.7 g 5-chloro-2-nitrobenzyl alcohol in 1 liter of toluene containing 20 ml. of pyridine is added 75 ml. of thionyl chloride (SOCl₂). The reaction mixture is stirred for 1.5 hours and permitted to stand overnight at room temperature. The product is freed of solvent, taken in methylene chloride and dried to afford 74.0 g. of 5-chloro-2-nitrobenzyl chloride.

The product produced in the preceding paragraph (37 g.) is refluxed with 13.5 g. sodium azide (NaN₃) in 1 liter of ethanol for a period of three hours. The solution is chilled, filtered and freed of solvent to afford 33.7 g. of 5-chloro-2-nitrobenzyl azide.

To the product of the preceding paragraph is added a molar excess of ethyl cyanoformate and the mixture is heated in a Teflon ® lined bomb for 30 hours, the product taken in methylene chloride and its volume reduced to about one third. The product is triturated with diethyl ether, dried in vacuo at room temperature for six hours to yield 30.6 g. (m.p. 133°–137° C.) of ethyl 1-(5-chloro-2-nitrobenzyl)-5-tetrazolcarboxylate.

The product of the preceding paragraph is dissolved in ethanol saturated with hydrochloric acid and the nitro group is reduced with iron powder to afford ethyl 1-(5-chloro-2-aminobenzyl)-5-tetrazolcarboxylate.

The product of the preceding paragraph (35.0 g.) is taken in 700 ml. methylene chloride to which 53 ml. of trimethylaluminum is added with stirring. 1 N hydrochloric acid is added. The methylene chloride phase is separated and the aqueous phase is extracted with methylene chloride. The combined organic extracts are dried, freed of solvent and the product recrystallized recrystallized from acetonitrile. The product is dried in vacuo at 82° C. for four hours to yield 22.5 g. (m.p. 260°–263.5° C.) of the title product.

Analysis for: $C_9H_6N_5OCl$;
Calculated: C, 45.87; H, 2.57; N, 29.72;
Found: C, 45.65; H, 2.70; N, 30.02.

EXAMPLE 2

5,10-Dihydro-11H-tetrazolo[5,1-c][1,4]benzodiazepine-11-one

2-Nitrobenzylchloride dissolved in ethanol is heated at reflux with a 10% molar excess of sodium azide for from six to eight hours. Insoluble salts are removed by filtration, the ethanol removed, and the resultant oil is dissolved in diethyl ether. Additional insoluble material is removed by filtration and 2-nitrobenzylazide is obtained as a pale yellow oil by removal of the diethyl ether.

The product of the preceding paragraph is heated with ethyl cyanoformate in a Teflon ® lined bomb for five to six hours at 145° C. The resultant semi-solid mass is chromatographed on silica gel with chloroform. The product is freed of solvent and recrystallized from benzene to afford ethyl 1-(2-nitrobenzyl)-5-tetrazolcarboxylate (m.p. 90°–92° C.) in 58% yield.

The product of the preceding paragraph is dissolved in ethanol saturated with hydrochloric acid and the nitro group is reduced with iron powder. The reaction mixture is stirred for one hour after the exothermic reaction, the reaction mixture is taken to dryness and diluted with water. The product is extracted with methylene chloride and recrystallized from acetone-water to afford ethyl 1-(2-aminobenzyl)-5-tetrazolcarboxylate in 83% yield.

To 75 mmol. of the product of the preceding paragraph in 500 ml. of methylene chloride under nitrogen, is slowly added 31 ml. of trimethylaluminium in hexane (25%, 77 mmol.). After one hour, 80 ml. of 1 N hydrochloric acid is added cautiously, the organic phase is separated and the aqueous phase is extracted with methylene chloride. The combined organic extracts are dried, evaporated, and the desired product is crystallized from ethyl acetate to yield 5,10-dihydro-11H-tetrazolo[5,1-c][1,4]benzodiazepine-11-one.

Alternatively, ethyl 1-(2-aminobenzyl)-5-tetrazolcarboxylate (8.0 g., 0.03 mol) in 200 ml. of dimethylformamide is added to 1.5 g. (0.03 mol) of 50% sodium hydride. The mixture is stirred overnight, poured into dilute hydrochloric acid and extracted with methylene chloride. Evaporation of the dried solvent gives a semisolid which is triturated with hexane and recrystallized from acetonitrile to yield 3.7 g. (56% of theory) of the 5,10-dihydro-11H-tetrazolo[5,1-c][1,4]benzodiazepine-11-one.

Analysis for: $C_9H_7N_5O$;
Calculated: C, 53.73; H, 3.51; N, 34.81;
Found: C, 53.33; H, 3.39; N, 35.17.

EXAMPLE 3

5,10-Dihydro-7-methyl-11H-tetrazolo[5,1-c][1,4]-benzodiazepine-11-one

Following the procedure of the preceding examples, with the exception that 5-methyl-2-nitrobenzylchloride is employed as the starting material, affords the corresponding 5,10-dihydro-7-methyl-11H-tetrazolo[5,1-c][1,4]benzodiazepine-11-one (m.p. 244°–247° C.) in 80% yield when recrystallized from ethanol.

Analysis for: $C_{10}H_9N_9O$,
Calculated: C, 55.81; H, 4.21; N, 32.54;
Found: C, 55.70; H, 4.35; N, 32.89.

EXAMPLE 4

5,10-Dihydro-7-nitro-11H-tetrazolo[5,1-c][1,4]-benzodiazepine-11-one

To 10.8 g. (54 mmol.) of the product of Example 2 in 135 ml. of sulfuric acid at 0° C. is added 2.1 ml. of 70% nitric acid. After 1.5 hours at 0° C. the reaction mixture is poured into ice water, the product is collected, triturated with hot acetonitrile, and then triturated with diethyl ether to give the crude prouduct, m.p. 276°–279° C. (11.3 g.; 85%). An analytical sample is recrystallized from dimethylformamide-methanol (m.p.) 283°–284° C.).

Analysis for: $C_9H_6N_6O_3$
Calculated: C, 43.90; H, 2.46; N, 34.14
Found: C, 43.86; H, 2.76; N, 34.42

EXAMPLE 5

5,10-Dihydro-8-chloro-11H-tetrazolo[5,1-c][1,4]-benzodiazepine-11-one

The title compound is produced following the procedure of Example 1 with the exception that as the initial reactant, 4-chloro-2-nitrobenzyl azide is employed. The product is recovered in 73% yield (m.p. 256°–259° C.) and recrystallized from methanol.

Analysis for: $C_9H_6N_5OCl$ ;
Calculate: C, 45.87; H, 2.57; N, 29.72;
Found: C, 45.79; H, 2.14; N, 29.69.

EXAMPLE 6

5,10-Dihydro-11H-tetrazolo[5,1-c][1,4]benzodiazepine-11-thione

A solution of 50 mmol. of the product of Example 2 and 20 mmol. of phosphorus pentasulfide in 120 ml. of pyridine is heated at 110° C. for one hour, poured into ice water, stirred for 0.5 hours and filtered. The solid product is washed well with water and then with hexane. Recrystallization from acetic acid affords an 80% yield of the title compound (m.p. 275°–277° C.).

Analysis for: $C_9H_7N_5S$
Calculated: C, 49.75; H, 3.25; N, 32.24
Found: C, 49.95; H, 3.30; N, 32.55

EXAMPLE 7

5,10-Dihydro-7-methyl-11H-tetrazolo[5,1-c][1,4]-benzodiazepine-11-thione

The procedure of Example 6 is repeated with the exception that the starting material is the product of Example 3 to provide an 86% yield of the title compound (m.p. 293°–296° C.) crystallized from acetic acid.

Analysis for: $C_9H_9N_5S$; Calculated: C, 51.93; H, 3.92; N, 30.28;
Found: C, 51.83; H, 3.77; N, 30.60.

EXAMPLE 8

5,10-Dihydro-8-Chloro-11H-tetrazolo[5,1-c][1,4]-benzodiazepine-11-thione

The title compound is produced following the procedure of Example 6 with the exception that as the starting material, the product of Example 5 is employed. The product is produced in an 83% yield by recrystallization from acetic acid (m.p. 284°–285° C.).

Analysis for: $C_9H_6N_5ClS$;
Calculated: C, 42.94; H, 2.40; N, 27.83;
Found: C, 42.95; H, 2.72; N, 27.86.

EXAMPLE 9

5,10-Dihydro-7-Chloro-11H-tetrazolo[5,1-c][1,4]-benzodiazepine-11-thione

The title compound is produced in 75% yield following the procedure of Example 6 except that the starting material is the product of Example 1. The product (m.p. 289°–290° C.) is recrystallized from acetic acid.

Analysis for: $C_9H_6N_5ClS$
Calculated: C, 42.94; H, 2.40; N, 27.83
Found: C, 43.02; H, 2.54; N, 28.00

EXAMPLE 10

11-Methylthio-5H-tetrazolo[5,1-c][1,4]benzodiazepine

To 30 mmol. of the product of Example 6 in 300 ml. of ethanol is added 33 ml. of 1 N sodium hydroxide followed by the slow addition of 54 mmol. of methyl iodide. After two hours the reaction mixture is evaporated to one fourth its volume, 100 ml. of water is added and the product is obtained by extraction into methylene chloride. The methylene chloride is removed by evaporation and the product is recrystallized from ethyl acetatehexane to afford an 89% yield (m.p. 105°–108° C.) of the title compound.

Analysis for: $C_{10}H_9N_5S$
Calculated: C, 51.93; H, 3.92; N, 30.28
Found: C, 51.75; H, 4.02; N, 29.88

EXAMPLE 11

7-Methyl-11-methylthio-5H-tetrazolo[5,1-c][1,4]benzodiazepine

The product is produced by following the procedure of Example 10 with the exception that the product of Example 7 is employed as the starting material. The product is obtained in 87% yield (m.p. 157°–160° C.) is crystallized from ethyl acetate.

Analysis for: $C_{11}H_{11}N_5S$;
Calculated: C, 53.85; H, 4.52; N, 28.55;
Found: C, 53.76; H, 4.56; N, 28.83.

Example 12

8-Chloro-11-methylthio-5H-tetrazolo[5,1-c][1,4]benzodiazepine

The title compound is produced in 71% yield following the procedure of Example 10 with the exception that the product of Example 8 is employed as the starting material. The product is recrystallized from ethyl acetate-hexane (m.p. 168°–170° C.).

Analysis for: $C_{10}H_8N_5SCl$;
Calculated C, 45.20; H, 3.03; N, 26.36;
Found: C, 45.08; H, 3.30; N, 26.22.

EXAMPLE 13

7-Chloro-11-methylthio-5H-tetrazolo[5,1-c][1,4]benzodiazepine

The title compound is produced following the procedure of Example 10 with the exception that the product of Example 9 is employed as the starting material. The product is obtained in a 77% yield (m.p. 131°–133° C.) and is recrystallized from ethyl acetate-hexane.

Analysis for: $C_{10}H_8N_5SCl$;
Calculated: C, 45.20; H, 3,03; N, 26.36;
Found: C, 45.46; H, 3.17; N, 26.63.

EXAMPLE 14

N-(1-methyl-4-piperidyl)-5H-tetrazolo[5,1-c][1,4]benzodiazepin-11-amine

To a solution of 5.0 g. (22 mmol.) of 11-Methylthio-5H-tetrazolo[5,1-c][1,4]benzodiazepine in 15 ml. of 4-amino-1-methylpiperidine is heated at 115° C. for 18 hours. The excess amine is evaporated and the resulting solid is triturated with water. Recrystallization from ethanol-water gives the title product in 49% yield (m.p. 112°–114° C.).

Analysis for: $C_{15}H_{19}N_7$;
Calculated: C, 60.58; H, 6.44; N, 32.98;
Found: C, 60.35; H, 6.50; N, 32.83.

EXAMPLE 15

N,N-dimethyl-N'-(5H-tetrazolo[5,1-c][1,4]benzodiazepin-11-yl)-1,3-propanediamine The title compound is prepared following the procedure of the preceding Example 14 with the exception that dimethylaminopropylamine is employed as the amine. The product is obtained in 78% yield (m.p. 148°–150° C. as the maleate salt) and is recrystallized from acetone-diethyl ether.

Analysis for: $C_{14}H_{19}N_7 \cdot C_4H_4O_4$;
Calculated: C, 53.85; H, 5.77; N, 24.43;
Found: C, 53.83; H, 5.76; N, 24.72.

EXAMPLE 16

7-Chloro-11-(4-methyl-1-piperazinyl)-5H-tetrazolo[5,1-c][1,4]benzodiazepine

The title compound is prepared following the procedure of Example 14 with the exception that N-methylpiperazine is employed as the amine and the product of Example 13 is employed as the initial reactant. The product is obtained in 80% yield (m.p. 220°–222° C.) crystallized from diethyl ether.

Analysis for: $C_{14}H_{16}N_7Cl$;
Calculated: C, 52.29; H, 5.07; N, 30.84;
Found: C, 52.60; H, 5.15; N, 30.71.

EXAMPLE 17

8-Chloro-11-(4-methyl-1-piperazinyl)-5H-tetrazolo[5,1-c][1,4]benzodiazepine

The title compound is produced following the procedure or Example 16 with the exception that the product of Example 12 is employed as the starting material. The product is obtained in 84% yield (m.p. 228°–230° C.) and recrystallized from diethyl ether.

Analysis for: $C_{14}H_{16}N_7Cl$;
Calculated: C, 52.29; H, 5.07; N, 30.84;
Found: C, 52.43; H, 5.12; N, 30.76.

EXAMPLE 18

7-Methyl-11-(4-methyl-1-piperazinyl)-5H-tetrazolo[5,1-c][1,4]benzodiazepine

The title compound is produced by the procedure of Example 16 with the exception that the product of Example 10 is employed as the starting material. The product is obtained in 65% yield (m.p. 280°–282° C. as the 1.5 HCl salt) and is recrystallized from isopropyl alcohol and diethyl ether.

Analysis for: $C_{15}H_{19}N_7 \cdot 1.5HCl$;
Calculated: C, 51.17; H, 5.86; N, 27.85;
Found: C, 50.67; H, 5.84; N, 28.06.

EXAMPLE 19

N'-(8-chloro-5H-tetrazolo[5,1-c][1,4]benzodiazepine-11-yl)-N,N-dimethyl-1,3-propanediamine The title compound is produced following the procedure of Example 15 with the exception that the product of Example 12 is employed as the starting material. The product is obtained in 87% yield (m.p. 135° C. (dec) as the hydrochloride hydrate).

Analysis for: $C_{14}H_{18}N_7Cl \cdot 2HCl \cdot H_2O$;
Calculated: C, 40.93; H, 5.40; N, 23.87;
Found: C, 40.95; H, 5.72; N, 24.08.

EXAMPLE 20

10,11-Dihydro-5H-tetrazolo[5,1-c][1,4]benzodiazepine

To 1.9 g. of lithium aluminum hydride in 250 ml. of tetrahydrofuran at reflux is added 10 g. of the product of Example 2. After six hours the mixture is cooled, 10 ml. of sodium hydroxide is added, the mixture is filtered and the filter cake is washed with hot tetrahydrofuran. The combined filtrates are evaporated. The resultant product is recrystallized from water to yield 3.6 g. (m.p. 128°–131° C.). The product is converted to the hydrochloride salt with isopropanolic hydrogen chloride-diethyl ether to provide a salt with m.p. 210°–212° C.

Analysis for: $C_9H_9N_5 \cdot HCl$;
Calculated: C, 48.32; H, 4.51; N, 31.31;
Found: C, 48.38; H, 4.45; N, 31.71.

What is claimed is:

1. A compound of the formula:

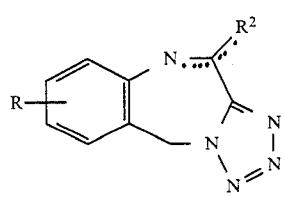

in which

R is hydrogen, halogen, alkyl of 1 to 6 carbon atoms, alkoxy of 1 to 6 carbon atoms, hydroxyl nitro or cyano; and $R^2$ is =O, =S, $H_2$, —$SCH_3$, or —$NR^4R^5$
where $R^4$ and $R^5$ are, independently, hydrogen, alkyl of 1 to 6 carbon atoms or dialkylaminoalkyl where each alkyl moiety has 1 to 6 carbon atoms, or $R^4$ and $R^5$ together form an alkylidene group of 4 to 6 carbon atoms, or, together with the nitrogen atom to which they are attached, they form the 4-morpholinyl moiety or a group of the formula:

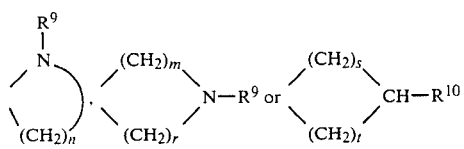

wherein $R^9$ is alkyl of 1 to 6 carbon atoms, aryl of 6 to 10 carbon atoms, hydroxyalkyl of 1 to 6 carbon atoms; aralkyl of 7 to 16 carbon atoms or alkoxyalkyl of 2 to 12 carbon atoms; $R^{10}$ is alkylamino of 1 to 6 carbon atoms or piperidino; n is one of the integers 3, 4 or 5; m is one of the integers 1 or 2; r is one of the integers 2 or 3; s is an integer from 0 to 6; t is an integer from 0 to 6; with the proviso that the sum of s and t is 3 to 6; and with the proviso that when R is chloro in 8-position, $R^2$ must be other than oxygen or sulfur; or a pharmaceutically acceptable salt thereof.

2. A compound of the formula:

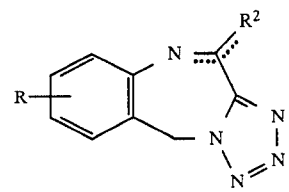

in which
R is hydrogen, chloro, methyl or nitro; and $R^2$ is =O, =S, $H_2$, —$SCH_3$, —$NHCH_2CH_2N<CH_3 <CH_3$,

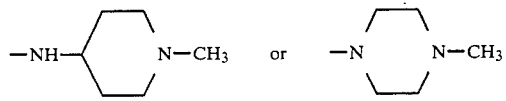

with the proviso that when R is chloro in 8-position, $R^2$ must be other than oxygen or sulfur; or a pharmaceutically acceptable salt thereof.

3. The compound of claim 1 which is 7-chloro-5,10-dihydro-11H-tetrazolo[5,1-c][1,4]benzodiazepine-11-one.

4. The compound of claim 1 which is 5,10-dihydro-11H-tetrazolo[5,1-c][1,4]benzodiazepine-11-one.

5. The compound of claim 1 which is 5,10-dihydro-7-methyl-11H-tetrazolo[5,1-c][1,4]benzodiazepine-11-one.

6. The compound of claim 1 which is 5,10-dihydro-7-nitro-11H-tetrazolo[5,1-c][1,4]benzodiazepine-11-one.

7. The compound of claim 1 which is 5,10-dihydro-11H-tetrazolo[5,1-c][1,4]benzodiazepine-11-thione.

8. The compound of claim 1 which is 5,10-dihydro-7-methyl-11H-tetrazolo[5,1-c][1,4]benzodiazepine-11-thione.

9. The compound of claim 1 which is 5,10-dihydro-7-chloro-11H-tetrazolo[5,1-c][1,4]benzodiazepine-11-thione.

10. The compound of claim 1 which is 11-methylthio-5H-tetrazolo[5,1-c][1,4]benzodiazepine.

11. The compound of claim 1 which is 7-methyl-11-methylthio-5H-tetrazolo[5,1-c][1,4]benzodiazepine.

12. The compound of claim 1 which is 8-chloro-11-methylthio-5H-tetrazolo[5,1-c][1,4]benzodiazepine.

13. The compound of claim 1 which is 7-chloro-11-methylthio-5H-tetrazolo[5,1-c][1,4]benzodiazepipe.

14. The compound of claim 1 which is N-(1-methyl-4-piperidyl)-5H-tetrazolo[5,1-c][1,4]benzodiazepin-11-amine.

15. The compound of claim 1 which is N,N-dimethyl-N'-(5H-tetrazolo[5,1-c][1,4]benzodiazepin-11-yl)-1,3-propanediamine.

16. The compound of claim 1 which is 7-chloro-11-(4-methyl-1-piperazinyl)-5H-tetrazolo[5,1-c][1,4]benzodiazepine.

17. The compound of claim 1 which is 8-chloro-11-(4-methyl-1-piperazinyl)-5H-tetrazolo[5,1-c][1,4]benzodiazepine.

18. The compound of claim 1 which is 7-methyl-11-(4-methyl-1-piperazinyl-5H-tetrazolo[5,1-c][1,4]benzodiazepine.

19. The compound of claim 1 which is N'-(8-chloro-5H-tetrazolo[5,1-c][1,4]benzodiazepine-11-yl)-N,N-dimethyl-1,3-propanediamine.

20. The compound of claim 1 which is 10,11-dihydro-5H-tetrazolo[5,1-c][1,4]benzodiazepine.

* * * * *